United States Patent [19]
Lorenzi et al.

[11] 4,063,157
[45] Dec. 13, 1977

[54] MAGNETIC TESTING DEVICE FOR INTERNAL SURFACES OF PIPE USING A MAGNETIZING MEANS AND EXPANDABLE MAGNETIZABLE MATERIAL WITHIN THE PIPE

[75] Inventors: Donald E. Lorenzi, Des Plaines; Richard C. Sabielny, McHenry; Kenneth W. Schroeder, Arlington, all of Ill.

[73] Assignee: Magnaflux Corporation, Chicago, Ill.

[21] Appl. No.: 774,919

[22] Filed: Mar. 7, 1977

Related U.S. Application Data

[63] Continuation of Ser. No. 652,428, Jan. 26, 1976, abandoned.

[51] Int. Cl.² ............................................. G01R 33/12
[52] U.S. Cl. .................................... 324/213; 324/220; 361/142
[58] Field of Search ............................. 324/37, 38, 41

[56] References Cited

U.S. PATENT DOCUMENTS

| 2,124,579 | 7/1938 | Knerr et al. | 324/37 |
| 2,622,125 | 12/1952 | Bender | 324/37 |
| 2,764,733 | 9/1956 | De Forest | 324/38 |
| 2,958,037 | 10/1960 | Riede et al. | 324/41 |
| 2,979,655 | 4/1961 | De Forest | 324/38 |
| 3,225,293 | 12/1965 | Wood et al. | 324/37 |

FOREIGN PATENT DOCUMENTS

| 1,237,864 | 6/1971 | United Kingdom | 324/37 |

*Primary Examiner*—Robert J. Corcoran
*Attorney, Agent, or Firm*—Brezina & Lund

[57] ABSTRACT

A magnetic testing device is provided in which a magnetic recording tape or paper is wrapped around the outside of a tubular pressure member of elastomeric material which is disposed between two circular end plates which form pole portions of a yoke having a central core extending between the end plates and having a coil wound thereon with a copper shield being disposed around the outside of the coil. The device is disposed in a pipe or the like and compressed air is supplied to inflate the pressure member and press the magnetic tape paper into intimate contact with the interior surface of the pipe while an AC current is supplied to the coil to apply a magnetic field to the pipe and to record a magnetic field pattern on the magnetic tape or paper.

1 Claim, 3 Drawing Figures

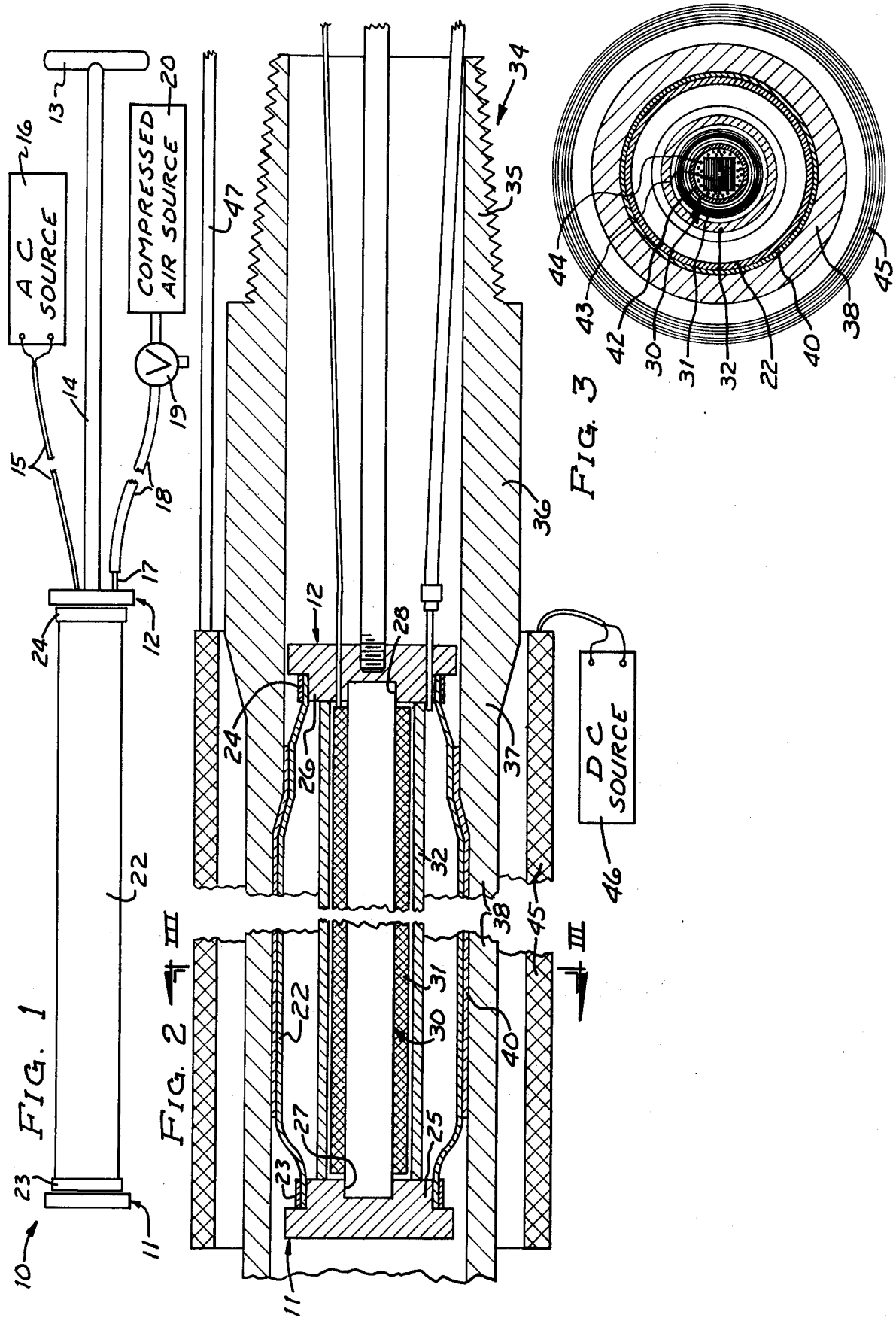

MAGNETIC TESTING DEVICE FOR INTERNAL SURFACES OF PIPE USING A MAGNETIZING MEANS AND EXPANDABLE MAGNETIZABLE MATERIAL WITHIN THE PIPE

This is a continuation of application Ser. No. 652,428, filed Jan. 26, 1976, now abandoned.

This invention relates to a magnetic testing device and more particularly to a device capable of inspecting internal surfaces of pipes or the like for defects. Testing can be performed readily and rapidly with the device and it is highly sensitive to provide indications which can be easily interpreted to provide accurate knowledge as to the character of the part tested.

BACKGROUND OF THE PRIOR ART

In prior proposed systems for the magnetic testing of parts for defects therein, difficulties have been experienced in testing of surface portions of a part which are irregular in contour or which are inside of a part to present difficulties with respect to access thereto. An example is drill pipe in which transverse fatigue cracks and corrosion pitting are oftentimes developed on the internal surface of the type especially in the end regions in which the pipe is formed with coupling portions to permit the end of one pipe section to be joined to the end of another. Prior art systems for testing of drill pipe and the like have been quite complicated, expensive, difficult to operate and not always reliable. Systems have been proposed for optical scanning which is not capable of detecting some types of serious defects, especially when the surface of the pipe is rusted or corroded. Systems have also been proposed using probes moved around on the inside of the pipe to scan the internal surface for defects, presenting problems especially with respect to obtaining the required scanning movement of the probe while maintaining the proper spacing relationship between the probe and the internal surface of the part.

There also have been prior art systems using a magnetic tape or other magnetizable material placed in contact with the surface of a part. Generally such systems have been designed for the testing of external or otherwise readily accessible surfaces. However, in the De Forest U.S. Pat. No. 2,764,733 issued Sept. 25, 1956, there is a suggestion in FIG. 6 of placing a tube inside a pipe, the tube being of an elastomeric material such as rubber with magnetizable particles such as iron or iron oxide particles dispersed therein and being inflated by compressed air to contact the internal surface of the part. The manner of magnetizing the part is not specifically disclosed.

SUMMARY OF THE INVENTION

This invention was evolved with the general object of overcoming the disadvantages of prior art systems and of providing a device for detection of inhomogeneities in parts which can be readily applied to testing of surfaces which are irregular in contour and not readily accessible.

Another object of the invention is to provide a device which is easy to operate and inexpensive to manufacture while providing an indication of inhomogeneities which can be readily and accurately interpreted.

A specific object of the invention is to provide a device for ready and accurate inspection of the interior surfaces of drill pipe and similar parts.

This invention is based, in part, upon the recognition of the problems involved with prior art systems and in the recognition that an arrangement similar to that shown in FIG. 6 of the aforementioned De Forest patent might be used for the testing of drill pipe or similar objects, with suitable additions thereto. An important feature of the invention is in the provision of a unitary device including a support structure which carries a pressure member to support the member with one surface of a flexible wall thereof opposite a surface portion of the part and with means for applying pressure against the opposite surface of the wall to press magnetizable material on the wall into intimate contact with the surface portion of the part. The support structure may also carry magnetizing means for developing a magnetic field in the surface portion of the part and to thereby develop in the magnetizable material localized magnetized portions corresponding to inhomogeneities in the portion of the part engaged thereby.

With this arrangement, a unitary device is provided which can be readily positioned in proper relationship to a part to perfor the testing thereof. The magnetizable material, preferably separate from the pressure member, can be removed and magnetic particles can be dispersed thereon to develop a visible pattern corresponding to the recorded flux pattern. Alternatively, a magnetic recording paper may be used to directly develop a visible pattern corresponding to the flux pattern. In either case, a record is obtained which can be inspected for an accurate and readily interpretable indication of the character of the part, after which the flux pattern may be erased, if desired, to permit re-use of the material.

Preferably and in accordance with a specific feature, compressed air or other pressurized fluid is used to press against the flexible wall of the pressure member to obtain the intimate contact between the magnetizable material and the surface of the part.

In accordance with another important feature, the device is arranged for testing an internal generally cylindrical surface portion of a part such as an end section of drill pipe. The flexible wall of the pressure member is preferably of tubular form and the support structure is adapted for insertion within the part to position the pressure member within the outer surface thereof opposite the generally cylindrical surface portion of the part to be tested.

In accordance with another feature, the magnetizing means includes a yoke of magnetic material having opposite pole portions positioned in proximity to spaced internal surface portions of the part on opposite sides of the surface portions engageable by the magnetic material, and a core portion is provided extending axially between the pole portions with a magnetizing coil wound thereon.

Another feature is in the provision of a generally cylindrical shield of conductive metal surrounding the magnetizing coil and extending between the pole portions.

A further feature is that in the alternative, or in addition, the magnetizing means includes a coil around the outside of the member tested, energized from a DC source.

This invention contemplates other objects, advantages and features which will become more fully apparent from the following detailed description taken in conjunction with the accompanying drawings.

BRIEF DESCRIPTION OF THE DRAWINGS

FIG. 1 is a side elevational view of a device constructed in accordance with the invention, auxiliary equipment being shown diagrammatically;

FIG. 2 is a longitudinal sectional view of the device of FIG. 1, also showing the device in operation, positioned within an end portion of a section of drill pipe; and FIG. 3 is a sectional view taken substantially along line IIII—III of FIG. 2.

DESCRIPTION OF A PREFERRED EMBODIMENT

Reference numeral 10 generally designates a testing device constructed in accordance with the principles of this invention. The device 10 is arranged to be disposed within a part to be tested such as an end portion of a section of drill pipe and includes a pair of circular end plates 11 and 12 which form pole portions of a yoke structure as hereinafter described with a handle 13 being connected to the end plate 12 through a rigid rod 14, the end of rod 14 being threaded into the end plate 12 or otherwise secured thereto. A cable 15 projects from the end plate 12 for connection to an AC source 16 and a tubular fitting 17 projecting from the end plate 12 is arranged for connection through a flexible tubing 18 to a valve 19 which is connected to a compressed air source 20, as diagrammatically illustrated.

A pressure member in the form of a sleeve 22 is provided having opposite ends sealingly secured to reduced-diameter portions of the end plates 11 and 12 by clamps 23 and 24. The member 22 is of an elastomeric material providing a flexible generally cylindrical wall.

In operation, a sheet of magnetizable tape or paper is wrapped around the outside of the member 22 and may be loosely held thereon by rubber bands or the like. Then the device is inserted into the end of a part to be tested, and the valve 19 is opened to supply compressed air into a space within the member 22 which is then inflated to press the magnetizable material into intimate contact with an internal surface portion of the pipe. Then a magnetizing current is applied from the source 16 and a magnetic field is developed extending longitudinally through the pipe between the end plate 11 and 12. As a result, a magnetic flux pattern is produced in the magnetizable material, which corresponds to the character of the internal surface portion of the pipe. Any cracks or other inhomogeneities will produce strongly magnetized localized portions. Then after cutting off the supply of current from the source 16, the valve 19 is moved to a position to release the pressure within the member 22 and the device is removed from the pipe. The magnetizable material is then removed and magnetic particles may be dispersed thereon to make the flux pattern visible or if the material is in the form of a magnetic recording paper, the pattern may be immediately viewed. It will be appreciated that the inspection can be performed quite easily and quite rapidly and a highly accurate indication of the character of the part is obtained.

Referring to FIG. 2, the end plates 11 and 12 include reduced diameter portions 25 and 26 to which the ends of the member 22 are secured by the clamps 23 and 24 and may further include sockets 27 and 28 which receive the opposite ends of a central magnetic core structure 30. A coil 31 is wound on the core structure 30 and is connected through the cable 15 to the AC source 16.

A split tube 32 of highly conductive metal, preferably copper, is disposed around the coil 31 between the end plates 11 and 12, in order to contain the magnetic flux lines and to minimize magnetic bridging. The provision of the tube 32 greatly increases the length of the section in which good inspection results are obtained.

The device is shown in FIG. 2 in an operative condition disposed within an end portion of a drill pipe section 34, which includes an externally threaded portion 35, an enlarged outside diameter portion 36 and a portion 37 between the portion 36 and a main portion 38 of the pipe section 34. The portions 34, 36 and 37 have the same internal diameter which is less than that of the main portion 38. The region depicted and a similar region at the opposite end of the pipe section are termed the "up-set" end regions of the drill pipe and it is in these regions that pipe failures occur. Stress reversals are a routine factor while drilling and the highest stress reversals are apparently localized near the up-set regions. As shown, when compressed air is supplied into the space within the member 22, it is inflated to press a magnetizable member 40 thereon into intimate contact with the facing internal surface portions of the pipe section 34. It is noted that because of the flexibility of the member 22, the device can accommodate irregular contours in the surface which it engages.

When current is applied to the magnetizing coil 31, magnetic flux passes from one of the end plates 11 and 12 to the other and longitudinally through the portion of the pipe in which the device is disposed. A flux pattern is thereby recorded by the magnetizable material corresponding to the character of the internal surface portion of the pipe.

A practical construction for the central core 30 is illustrated in the cross-sectional view of FIG. 3. A tube 42 is provided which may be of an insulating material and a stack of rectangular laminations 43 is disposed within the tube 42 with small rods 44 being inserted to fill in the spaces between the outer faces of the stack of laminations 43 and the internal cylindrical surface of the tube 42. Other core constructions might be used but a construction similar to that illustrated is preferred. It produces results superior to those obtained with a solid core or a core consisting of rods only.

Excellent results can be obtained with a device constructed in accordance with the invention. For example, a device has been tested having a construction as shown in the drawings with an overall length of 21⅜ inches from the outer face of one end plate to the outer end face of the other, the components having substantially the same proportionate dimensions as shown in the drawing. The end plates 11 and 12 were of hot rolled steel. The core included 0.023 inches by 1 inch by 20 inch laminations 43, rods 44 having a diameter of 1/16 inches and a length of 20 inches, disposed in a tube having an internal diameter of 1.407 inches and an external diameter of 1.876 inches, also with a length of 20 inches. The coil consisted of 620 turns in two layers of No. 16 copper wire. Excellent results were obtained using alternating current excitation such as to provide 5500 ampere turns. Slots milled into the internal surface of the pipe for test purposes and having a depth of 0.02 inches produced strong indications on a magnetic tape material and comparable results can be obtained on a magnetic paper material.

The provision of the conductive tube or shield 32 is important. Without the shield, good inspection results were confined to approximately plus or minus 3 inches each side of the core center. With the addition of the copper shield, good inspection coverage was extended to within 2 inches from either of the end plates.

Close fitting between the end plates and the internal pipe surfaces does not appear to be critical. Good inspection results were obtained using gaps as large as 0.25 inches. If desired, ring collars can be slipped over the end plates to accommodate pipe having a larger internal diameter.

The alternating current excitation with the magnetizing means on the inside of the pipe results in a concentration of the magnetic flux in the internal surface of the pipe and is preferable, especially when the pipe has a relatively thick wall. It is possible, however, to use DC excitation of the coil 31 or a combination of DC and AC excitation. In addition, a coil 45 may be placed around the pipe, as shown in FIGS. 2 and 3, coil 45 being connected to a DC source 46. Coil 45 may be connected to the handle 13 through a rod 47 to be moved with the assembly, it being important that the coil extend for at least the full length of the portion of the pipe with which the magnetizable material is engaged.

The coil 45 is especially advantageous in the testing of thin-walled members and in devices especially designed for such purpose, the internal coil 31 and associated core 30 and shield 32 may be eliminated it being then only necessary to provide supporting structure for the member 22.

It will be understood that modifications and variations may be effected without departing from the spirit and scope of the novel concepts of this invention.

We claim as our invention:

1. A device for magnetic testing of pipe, comprising: a tubular member of flexible material, support means for said pressure member including an elongated rigid central portion extending axially within said pressure member and a pair of end portions on opposite ends of said central portion, and seal means securing opposite ends of said pressure member to said end portions of said support means, said pressure member being arranged to receive and support a sheet of magnetizable material wrapped therearound, said device being insertable to a stationary portion within a pipe to position a sheet of magnetizable material wrapped on said pressure member in alignment with a portion of the pipe, magnetizing means operable with said device in said stationary position for applying a magnetizing field through substantially the full length of said portion of the pipe and substantially uniform throughout said portion, said support means being in the form of a yoke of magnetic material including an elongated core portion forming said central portion and a pair of circular pole portions at opposite ends of said core portion and forming said pair of end portions, said pole portions having generally cylindrical peripheral surfaces on a common axis coincident with a central longitudinal axis of said core portion, said magnetizing means comprising a magnetizing coil wound on said core portion, a split cylindrical shield of conductive material extending between said pole portions arond said magnetizing coil, means operable with said device in said stationary position for applying a burst of alternating current to said magnetizing coil, said split cylindrical shield being effective to obtain a uniform longitudinal field in said portion of the pipe and a uniform relationship between the size of inhomogeneities and the intensity of leakage fields in said portion of the pipe, and means operable with said device in said stationary position for supplying pressurized fluid into the space within said pressure member for inflating said pressure member and pressing a sheet of magnetizable material wrapped therearound into intimate contact with the inner surface of said portion of the pipe to record on said sheet localized leakage fields corresponding to inhomogeneities in said portion of the pipe.

* * * * *